United States Patent
Ghammraoui et al.

(10) Patent No.: US 9,285,329 B2
(45) Date of Patent: Mar. 15, 2016

(54) METHOD OF ANALYSING A SAMPLE OF MATERIAL BY DIFFRACTOMETRY AND ASSOCIATED DIFFRACTOMETER

(71) Applicant: COMMISSARIAT A L'ENERGIE ATOMIQUE ET AUX ENERGIES ALTERNATIVES, Paris (FR)

(72) Inventors: Bahaa Ghammraoui, Liban (LB);
Joachim Tabary, Grenoble (FR);
Caroline Paulus, Grenoble (FR)

(73) Assignee: Commissariat A L'Energie Atomique et Aux Energies Alternatives, Paris (FR)

( * ) Notice: Subject to any disclaimer, the term of this patent is extended or adjusted under 35 U.S.C. 154(b) by 77 days.

(21) Appl. No.: 14/368,748

(22) PCT Filed: Dec. 26, 2012

(86) PCT No.: PCT/FR2012/053080
§ 371 (c)(1),
(2) Date: Jun. 25, 2014

(87) PCT Pub. No.: WO2013/098520
PCT Pub. Date: Jul. 4, 2013

(65) Prior Publication Data
US 2014/0348298 A1 Nov. 27, 2014

(30) Foreign Application Priority Data

Dec. 28, 2011 (FR) .................................. 11 62497
Sep. 20, 2012 (FR) .................................. 12 58851

(51) Int. Cl.
*G01N 23/207* (2006.01)
*G01N 23/20* (2006.01)
(Continued)

(52) U.S. Cl.
CPC ...... *G01N 23/2076* (2013.01); *G01N 23/20091* (2013.01); *G01T 1/366* (2013.01); *G21K 1/02* (2013.01); *G01N 2223/501* (2013.01)

(58) Field of Classification Search
CPC .............. G01N 23/207; G01N 23/223; G01N 23/2076; G01N 23/20; G01N 23/2252; G01N 23/20091; G01N 23/083
See application file for complete search history.

(56) References Cited

U.S. PATENT DOCUMENTS 5,007,072 A   4/1991  Jenkins
7,113,566 B1 * 9/2006  Peled .................... G01N 23/20
                                                378/160
(Continued)

FOREIGN PATENT DOCUMENTS

FR            2956216 A1    8/2011

OTHER PUBLICATIONS

Ordavo, I., et al. "A new pnCCD-based color X-ray camera for fast spatial and energy-resolved measurements", Nuclear Instruments & Methods in Physics Research. Section A: Accelerators, Spectrometers, Detectors, and Associated Equipment, Elsevier BV, North Holland, Netherland vol. 654, No. 1, May 29, 2011, pp. 250-257.

(Continued)

*Primary Examiner* — Hoon Song
(74) *Attorney, Agent, or Firm* — Brinks Gilson & Lione

(57) ABSTRACT

A method for analyzing a sample by diffractometry and a diffractometer, where the diffractometer includes a collimated source, a detection collimator, and a spectrometric detector, the detection axis of the detector and the collimator form a diffraction angle with the central axis of an incident beam and an energy spectrum is established for each pixel of the detector. The measured spectra are readjusted by a change in variable that takes into account the energy of the scattered radiation and the angle of observation. The measured are combined and a check is made on the implementation of at least one multi-material criterion representative of the presence of a plurality of layers of materials and groups of pixels are formed according to the results of this check, where each group corresponds to a single layer of material and the measured spectra obtained for the pixels of the group are combined.

25 Claims, 9 Drawing Sheets

(51) Int. Cl.
*G01T 1/36* (2006.01)
*G21K 1/02* (2006.01)

(56) References Cited

U.S. PATENT DOCUMENTS

2004/0131151 A1* 7/2004 Berman .................. G01N 23/20
378/70
2006/0140340 A1 6/2006 Kravis 2008/0008292 A1* 1/2008 Krmar .................... A61B 6/482
378/89

OTHER PUBLICATIONS

Harding et al. "X-ray diffraction imaging-A multi-generational perspective", Applied Radiation and Isotopes, Elsevier, Oxford, GB, vol. 67, No. 2, Feb. 1, 2009, pp. 287-295.
International Search Report of PCT/FR2012/053080 dated May 3, 2013, 6 pages.

* cited by examiner

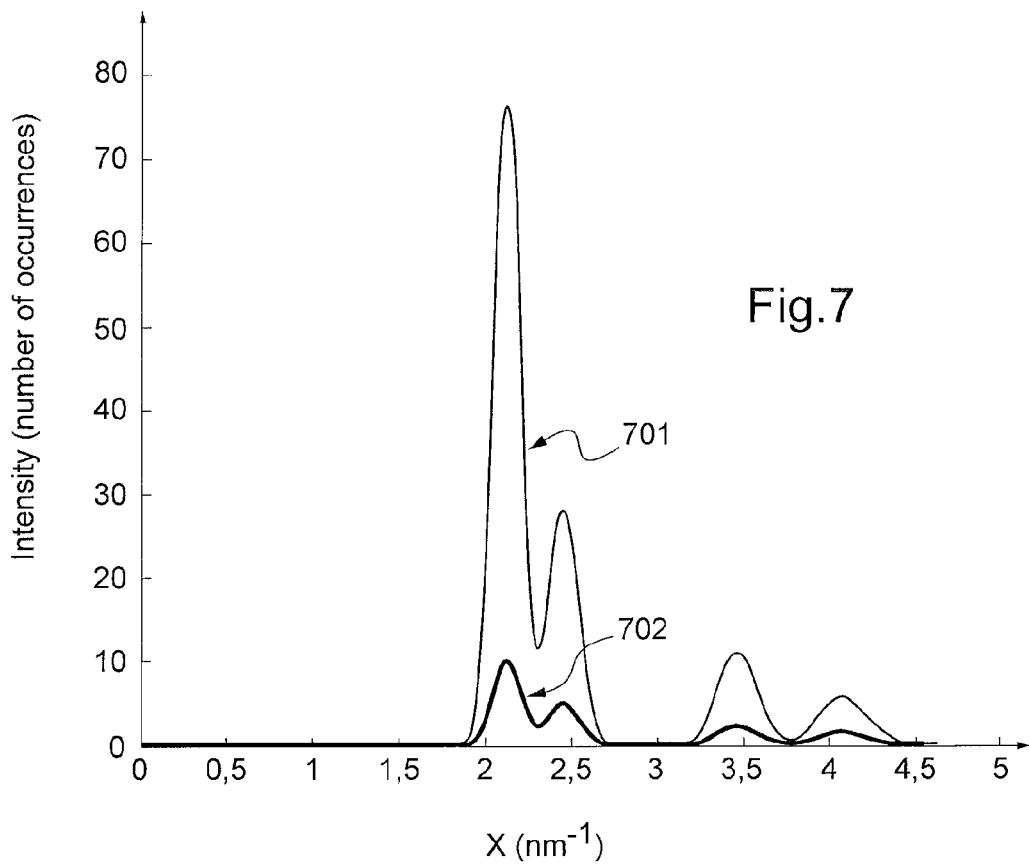
Fig.7
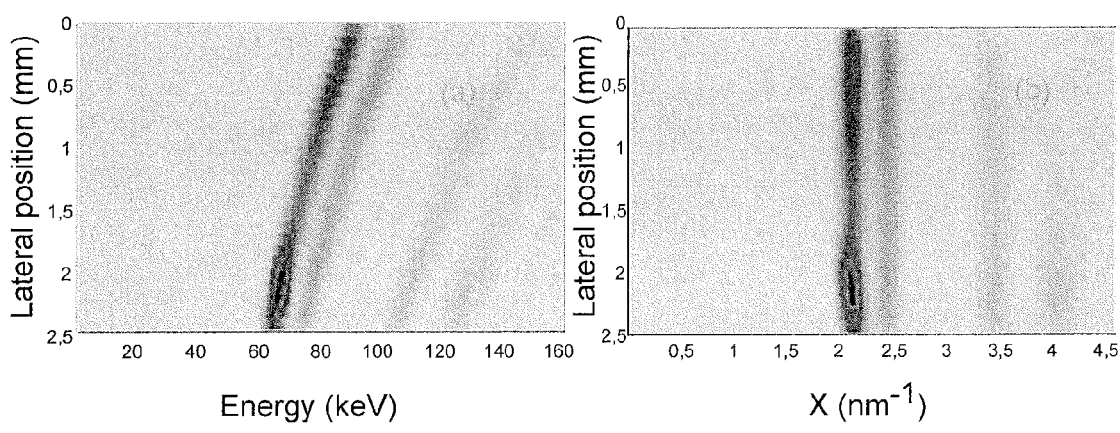
Fig.8a
Fig.8b
Fig. 8

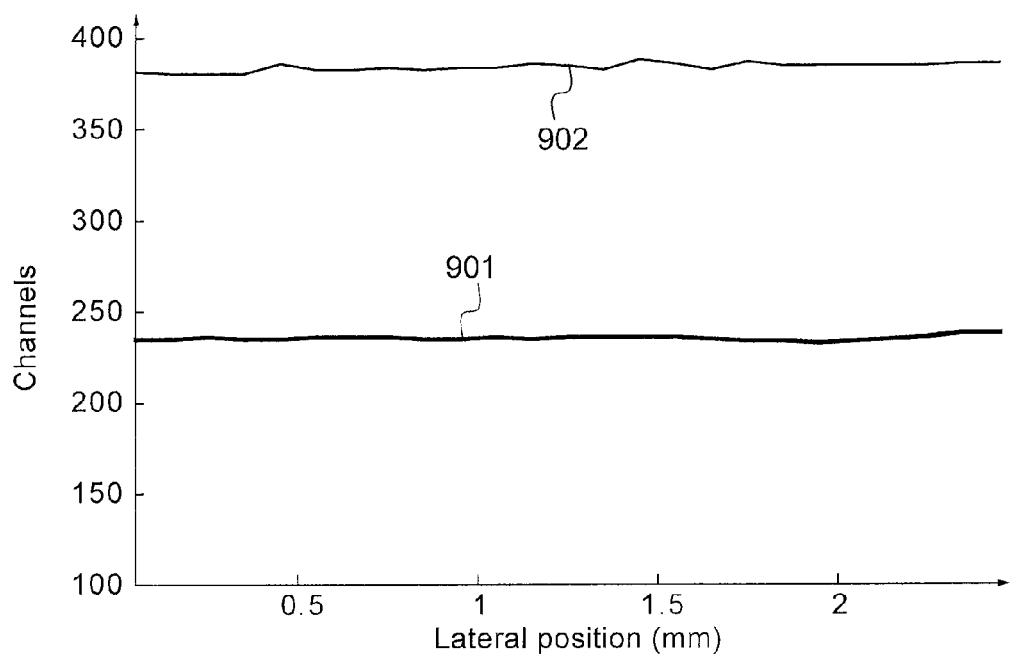
Fig.9
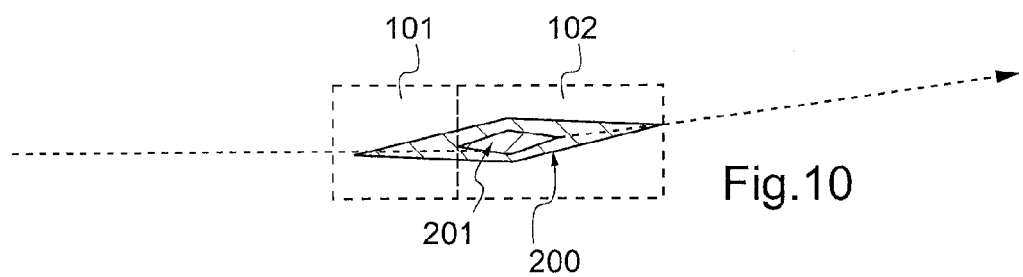
Fig.10
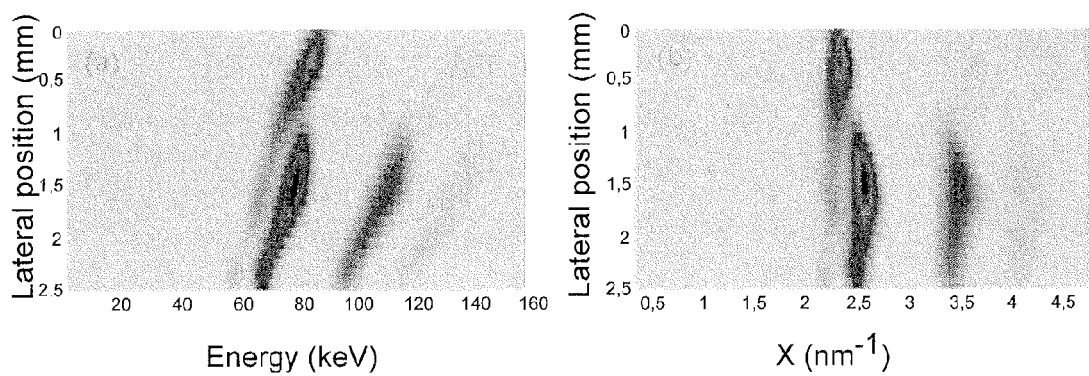
Fig.11a　　　　　　　　　　　Fig.11b
Fig. 11

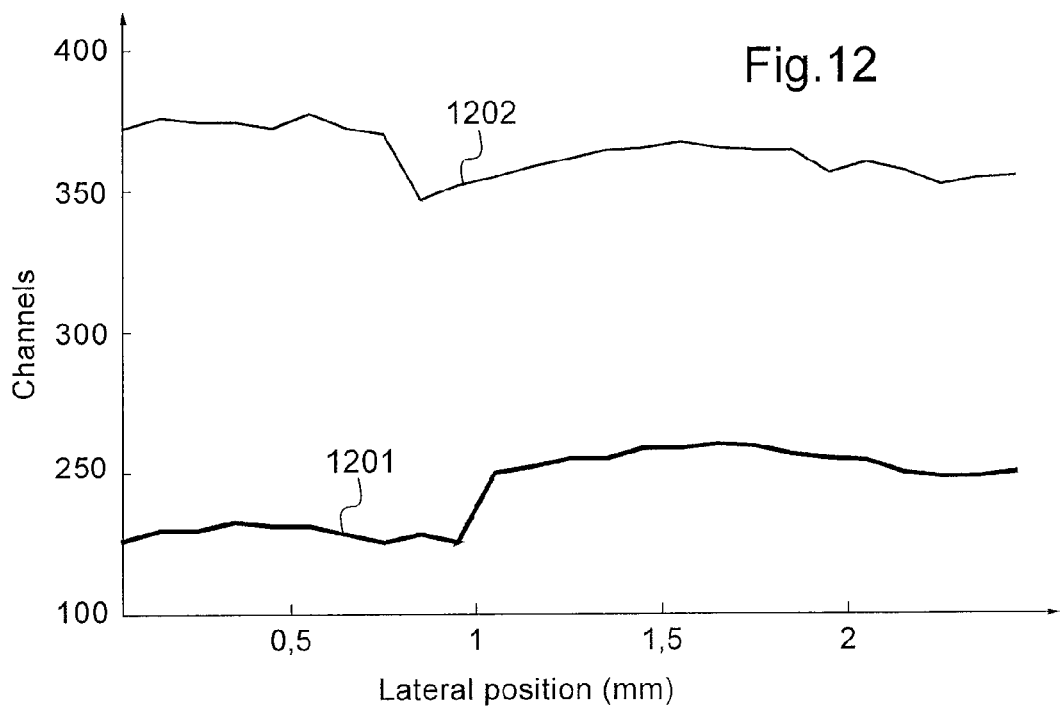
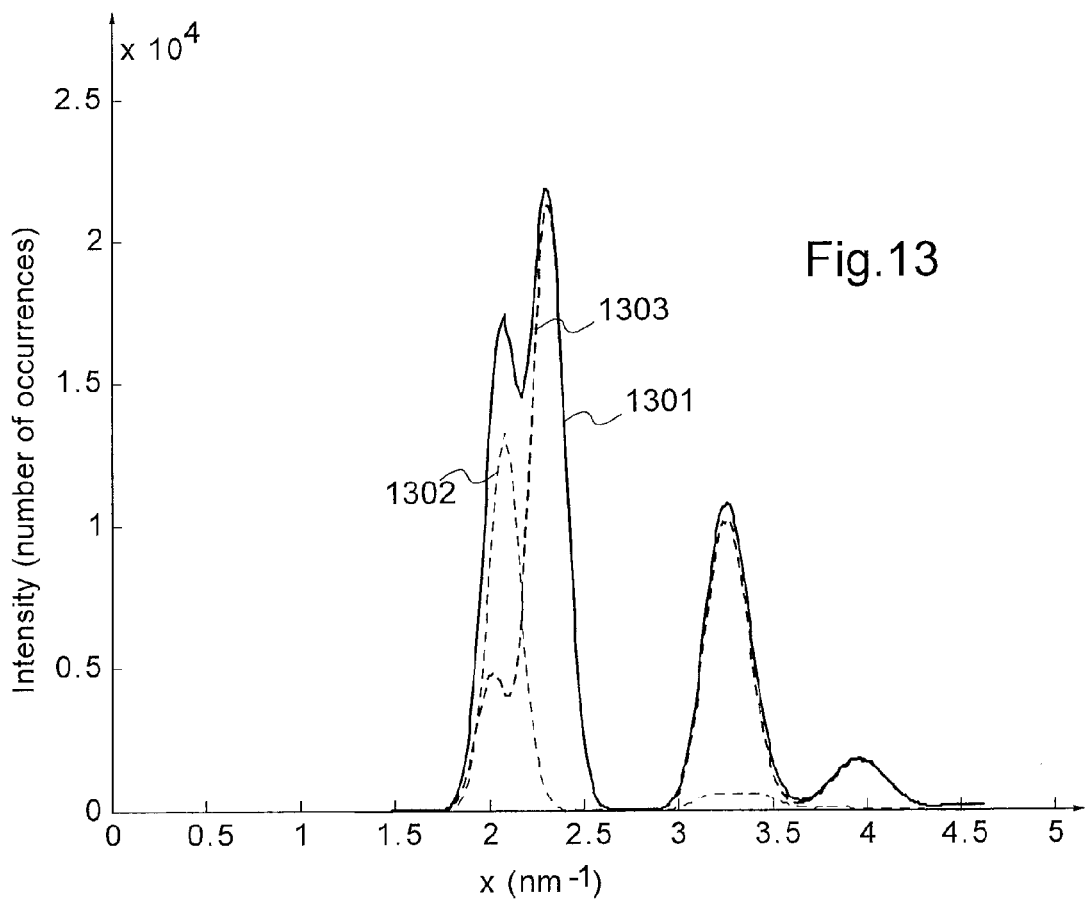

METHOD OF ANALYSING A SAMPLE OF MATERIAL BY DIFFRACTOMETRY AND ASSOCIATED DIFFRACTOMETER

This application is a U.S. nationalization of PCT Appl. No. PCT/FR2012/053080, filed Dec. 26, 2012 and claims priority to French Patent Appl. No. 1162497, filed Dec. 28, 2011, the disclosures of which are incorporated by reference herein.

TECHNICAL FIELD

The present invention concerns a method of analyzing a material by diffractometry, and an associated diffractometer.

BACKGROUND

It is known to use diffractometry to detect certain crystalline substances such as most explosives or numerous other dangerous or illegal structures. Within a crystal, which is an arrangement of atoms, elastically scattered electromagnetic waves interfere with each other to give scattering which is coherent at the scale of the crystal. When those interferences are constructive, they may be detected by the measurement of a diffracted ray and by the identification of the diffraction peaks. Thus, the constructive interferences are located by an appearance of diffraction peaks (or Bragg peaks) in the radiation diffused by a material.

To know whether a given crystalline substance is contained in a material, it is thus known to:
irradiate a sample of the material using an incident beam with a central axis X, emitted by a source, and to study the diffracted radiation using a detection device comprising a detector, termed spectrometric detector, adapted to establish an energy spectrum of the radiation diffused at a given scatter angle, that is to say a detector comprising
  a detector material, which, on the near side to the sample of material, presents a plane termed detection plane, and
  means, termed spectrometry measurement means, adapted to measure an energy released by each interaction of a photon with the detector material and to establish at least one energy spectrum, denoted S(E). A collimator, termed detection collimator, associated with the detector, the detector and the detection collimator being arranged so as to have a detection axis D, the detection axis D forming a diffraction angle θ with the central axis X of the incident beam.

It is to be noted that an energy spectrum illustrates the energy distribution of radiation in the form of a histogram representing the number of photon interactions in the material (along the y-axis) according to the released energy (along the x-axis). Generally, the energy axis is discretized into channels of width 2 δE, a channel Ci corresponding to the energies comprised between Ei−δE and Ei+δE.

The various peaks obtained on an energy spectrum of a radiation that is scattered, at an angle θ, are characteristic of the material analyzed, since the scattered radiation participating in the constructive interferences satisfies the following equation:

$$E_{hkl} = n\frac{hc}{2d_{hkl}\sin(\theta/2)}$$

with:
$d_{hkl}$: interplanar spacing between the crystallographic planes of the irradiated crystal;

θ: scatter angle, that is to say the angle formed between the scattered ray analyzed and the beam that is incident on the irradiated crystal
h: Planck's constant
c: the speed of light
n: the order of the interference.

This property is exploited in well-known methods, designated by the acronym EDXRD or "Energy Dispersive X-Ray Diffraction".

WO2008/142446 describes a method of determining the composition of an object by the spectrometric detection of an object irradiated by x-ray radiation. In the description of the prior art of WO2008/142446, reference is made to baggage checking. The method described comprises the following steps:
  irradiating the object, particularly for example using x-ray radiation,
  detecting the intensity transmitted through the object using a spectrometric detector. It is to be noted that the radiation studied here is the radiation transmitted by the sample of material and is not diffracted; in other words, the detection axis D coincides with the axis X of the incident beam,
  selecting energy bands in the transmitted spectrum, and establishing transmission quantities in each of those bands, and
  comparing at least two of said obtained quantities.

According to a first embodiment, it is sought to identify the material by detecting a Bragg detection signature. For this, a discontinuity in the transmitted intensity is revealed, at a given energy, or at least within a narrow energy band. This discontinuity is assumed to correspond to a localized drop in the amplitude of the transmitted signal under the effect of elastic scattering (Bragg diffraction) in the crystal lattice of the material analyzed. This scattering only occurs for certain discrete incident energies Ei and it is considered that in the neighborhood of that energy, the transmitted signal decreases. Thus, by comparing the intensity of the signal transmitted at that energy in a narrow energy band centered on Ei with the signal transmitted at another energy, the presence of a particular material is detected. In other words, in this application, analysis is made of the radiation transmitted by the object, and in particular of the discontinuities in its energy spectrum on account of Bragg diffraction.

US20060140340 describes a device for identifying illicit or dangerous substances, comprising:
  an x-ray source (2) associated with a primary collimator (3) delivering a beam of rectangular cross-section striking an inspection volume (6),
  an energy resolving energy detector (11) associated with a secondary collimator (10), which energy detector (11) provides an energy spectrum of the radiation diffracted at an angle θ by the inspection volume,
  a spatially resolving detector (13), which measures the intensity of the transmitted radiation, and
  a conveyor belt 8.

FIG. 4a of US20060140340 illustrates a first simulation with a sufficiently long acquisition time to give a good signal-to-noise ratio, but too long to envision the use of the method for detecting dangerous or illicit products in baggage. A second simulation carried out with a shorter acquisition time (compatible with the envisioned application, i.e. the detection of dangerous or illicit products in baggage) provides a signal of which the signal-to-noise ratio is low and leads to FIGS. 6a to 6c of US20060140340 being obtained, which are not possible to exploit.

To solve this problem, US20060140340 instructs to acquire diffraction data at a plurality of diffraction angles, either by moving the energy detector along a rail (12) in an arc of a circle centered on the source, or by using a plurality of detectors disposed at different diffraction angles. Each spectrum obtained is first of all corrected using a correction derived from a dual energy detection method. Next, the range of energies in each spectrum is divided into a plurality of narrower energy ranges. Each narrow energy range corresponds to a particular value of the momentum transfer. A diffraction model is then obtained by adding, point by point, the data substantially corresponding to the same momentum transfer values in the different spectra. The diffraction models so obtained for the two simulations (long and short acquisition time) are represented in FIGS. 5b and 7b, both of which can be exploited.

The first solution proposed by US20060140340, consisting of moving the detector along a circular rail, has the negative consequence of multiplying the processing time by the number of acquisitions carried out, which is not desirable for the application concerned. The second solution (increasing the number of detectors) leads to a bulky and costly diffractometer.

The technique of analysis by diffractometry, and more generally by spectrometry, requires the employment of a spectrometric detector that is sufficient energy resolving to enable the separation and the identification of the different characteristic peaks linked to the crystalline materials of the sample.

Generally, a Germanium type detector is used. This type of detector provides very attractive energy resolution but it must be cooled to very low temperatures, by complex and/or costly methods (thermoelectric cooling or cooling by a tank of liquid nitrogen). Also, the analysis devices employing such a detector are very bulky.

The recent emergence of spectrometric detectors capable of being used at ambient temperature, such as detector types implementing CdTe, CdZnTe, or scintillator materials (older technologies), provides an attractive alternative to the Germanium detectors. To be precise, these detectors are compact, not cooled and less costly. However, their performance in terms of energy resolution is still less than that obtained with the Germanium detectors.

SUMMARY

The invention is directed to mitigating these drawbacks by providing a method and device of which the energy resolution is improved, in order to obtain a clearer separation of the diffraction peaks for a better identification of materials.

In diffractometry, two parameters are essential to obtain a reliable and effective detection system: energy resolution and sensitivity. As always, these two parameters vary inversely: the improvement of one is accompanied by the degradation of the other. The gain in energy resolution obtained by virtue of the method and the device according to the invention makes increasing the sensitivity possible, while keeping a very satisfactory energy resolution. To improve the sensitivity, it suffices to increase the opening of the detection collimator in order to collect more signal. But the observed field (or inspection volume, defined as being the volume, in the sample of material, delimited by the incident beam and further delimited by the solid angle by which the detector sees the sample of material—that is to say the solid angle delimited by the opening of the detection collimator and the detection plane of the detector) is then greater, with an increased risk of superposition of materials, which may complicate the interpretation of the spectra obtained.

In a preferred version, the invention is directed to solving this additional problem by providing a method and a device which are particularly adapted to the analysis of samples comprising several layers of materials.

In this context, the invention provides a method of analyzing a sample of material by diffractometry, wherein:
a diffractometer is used which comprises a source adapted to emit an incident beam with a central axis X, a detector comprising
  a detector material, which, on the near side to the sample of material, presents a plane termed detection plane,
  means, termed spectrometry measurement means, adapted to measure an energy released by each photon interaction with the detector material and to establish at least one energy spectrum, denoted S(E);
  a collimator, termed detection collimator, associated with the detector, the detector and the detection collimator being arranged so as to have a detection axis D forming a diffraction angle θ with the central axis X of the incident beam,
the sample is irradiated with the incident beam, and
a plurality of energy spectra are established, a combination of which is carried out.

The method according to the invention is characterized in that:
the detector used is a detector qualified as a pixelated detector, comprising means for locating an interaction of a photon with the detector material, making it possible to define a partition of the detector in virtual pixels, and making it possible to associate one of said virtual pixels with each photon interaction;
an energy spectrum Si(E), termed measured spectrum, is established for each virtual pixel of the detector,
the combination relates to spectra measured for different virtual pixels of the detector.

In all that follows:
"diffraction plane" is used to mean a plane defined by the central axis of the incident beam X and the detection axis D;
"transverse direction" is used to mean a direction orthogonal to the detection axis D and contained in the diffraction plane (X, D); and
"lateral position Yi of a pixel Pi of the detector" is used to mean a coordinate of the virtual pixel Pi in the transverse direction.

In a preferred embodiment, the detector used according to the invention is pixelated in the detection plane, that is to say that its means of location make it possible to define a partition of the detection plane in virtual pixels along at least one pixelation direction contained in the detection plane, which pixelation direction is advantageously the transverse direction. Advantageously, the location means make it possible to define a partition of the detection plane in virtual pixels in two orthogonal directions in said detection plane.

This preferred form does not exclude the possibility of using a pixelated detector within the thickness, of which the location means make it possible to define a partition of the detector material in one direction, termed thickness direction, which is orthogonal to the detection plane. It is also possible to use a pixelated detector both in the detection plane and within the thickness.

A detector usually comprises a plurality of physical pixels, each physical pixel corresponding to a circuit for charge collection by an electrode. As defined above, the detector used according to the invention is pixelated virtually, that is to say using an item of location information for location, within each physical pixel, of a photon interaction taking place in alignment with that physical pixel. It is for example possible to determine the coordinates (x, y) of the barycenter of the cloud of charges produced by an interaction, on the basis of electrical signals simultaneously generated by that interaction on a plurality of adjacent anodes. This approach makes it possible to divide each physical pixel into a plurality of virtual pixels, the dimensions of which are less. It is thus considered that the interaction has been detected solely by the virtual pixel corresponding to the coordinates of the barycenter.

The use of a pixelated detector with virtual pixels and the combination of the energy spectra obtained make it possible to increase the angular resolution (by refining the diffraction angle observed by a pixel) while maintaining the intensity and the signal-to-noise ratio which would have been detected by a known detector. Thus, the energy resolution of the spectrum is improved, relative to the resolution of a spectrum obtained in the same geometrical configuration using a non-pixelated detector.

To be precise, the various virtual pixels of the detector according to the invention observe different parts of the inspection volume, with observation angles $\theta_i$ that are slightly different, those parts overlapping. The angular range which would be observed by a pixel, termed full pixel, covering the entirety of the detection plane, is much wider than the angular range observed by each pixel of the detector according to the invention. In other words, the angular resolution of the diffractometer according to the invention is much better than the angular resolution of the full pixel and thus of the known diffractometers. However, the inventors have shown that the energy resolution of a diffraction spectrum depends not only on the detectors own energy resolution, but also on the angular resolution, given by the collimation geometry. Therefore, the use of a detector that is virtually pixelated (that is to say a detector of which the pixels are of very small size) and the combination of the energy spectra obtained make it possible to improve the final energy resolution.

Advantageously and according to the invention, the pitch between two adjacent pixels in the transverse direction is: less than or equal to 0.5 mm (difference between $Y_{i+1}$ and $Y_i$) and preferably less than 0.2 mm, or less than or equal to 0.2° (difference between $\theta_{i+1}$ and $\theta_i$), and preferably less than 0.1°. Advantageously, and according to the invention, the method comprises, prior to the step of combining the spectra, a step of adjusting the measured spectra, in which each measured spectrum is expressed according to a new variable which takes into account the energy of the scattered radiation and the angle of observation $\theta_i$ of the corresponding pixel. An adjusted spectrum is thus obtained for each measured spectrum, that is to say for each virtual pixel of the detector. The step of combining spectra in this case concerns the adjusted spectra. These latter are preferably combined by an arithmetic operation.

Thus, in general terms, the method comprises:

the definition of a new variable taking into account the wavelength $\lambda$ or the energy E of the scattered radiation as well as the observation angle $\theta_i$;

the transformation of the measured spectra according to that new variable; and an arithmetic operation on the spectra transformed at the preceding step.

For example:

in the adjusting step, for each pixel, a spectrum $S_i(x)$ is established which is adjusted according to momentum transfer based on the energy spectrum measured for said pixel by performing a change in variable by virtue of the following formula:

$$x = \frac{\sin(\theta_i/2)}{\lambda} = \frac{E\sin(\theta_i/2)}{hc},$$

where $\theta_i$ designates the observation angle corresponding to the pixel Pi of row i that is to say the angle between the axis X of the incident beam and the axis Di passing by the center of the pixel Pi and the center of the detection collimator, and $\lambda$ is the wavelength corresponding to the energy E; in the combining step, a sum is calculated of all of or of some of the momentum transfer spectra so established.

The variable change provided according to the invention makes it possible to directly sum (or more generally, to combine arithmetically) the spectra $S_i(x)$ corresponding to different virtual pixels and thus gives a method of combining the energy spectra which is extremely simple, which may be implemented using computing means with low energy and memory requirements.

The invention also relates to a diffractometer adapted to implement the method according to the invention. In particular, the invention provides a diffractometer comprising:

a source adapted to emit an incident beam with a central axis X, a detector comprising a detector material, which, on the near side to the sample of material, presents a plane termed detection plane, means, termed spectrometry measurement means, adapted to measure an energy released by each photon interaction with the detector material and to establish at least one energy spectrum, denoted S(E);

a collimator, termed detection collimator, associated with the detector, the detector and the detection collimator being arranged so as to have a detection axis D forming a diffraction angle $\theta$ with the central axis X of the incident beam, and spectra combining means.

The diffractometer according to the invention is characterized in that:

the detector is a pixelated detector, according to the definition provided above (detector with virtual pixels);

the spectrometry measuring means are adapted to establish an energy spectrum measured for each virtual pixel of the detector; and the combining means are adapted to combine energy spectra measured for different virtual pixels of the detector.

Advantageously and according to the invention, the diffractometer comprises computing means, termed adjusting means, adapted to establish, for each virtual pixel of the detector, a spectrum adjusted according to momentum transfer on the basis of the energy spectrum measured for said pixel by change of variable using for example the formula indicated supra, the combining means then being adapted to sum, or more generally, to arithmetically combine, adjusted spectra so established.

Advantageously, the method and the diffractometer according to the invention have one or more of the following features, all the possible combinations being in accordance with the invention:

the detector is of the type with a detector material of semiconductor, which does not exclude the possibility of using a detector of the scintillator-based detector type. Semiconductor-based detectors are preferred for their better energy resolution and for their smaller bulk.

the source is a polychromatic source;

the source delivers radiation of which the maximum energy is comprised between 10 and 1000 keV, preferably between 10 and 200 keV;

the diffractometer comprises a collimator, termed source collimator, associated with the radiation source;

the source collimator is qualified as narrow according to an axis Y of the diffraction plane which is orthogonal to the axis X of the incident beam and is open along an axis Z which is orthogonal to the diffraction plane;

the source collimator is a collimator with a single rectangular slot;

the source collimator has a thickness (dimension along the axis X of the incident beam) of 100 mm and slot height (dimension along the axis Y) of 0.10 mm;

the diffraction angle θ is small; it is preferably comprised between 2° and 10°, preferably between 3° and 6°. The observation of the diffraction phenomenon is clearest at a small angle, since coherent scatter predominates for a small momentum transfer (the momentum transfer being proportional to $\sin(\theta/2)$).

the detection collimator used is a collimator with a single rectangular slot;

The detection collimator is a detector qualified as narrow collimator in the transverse direction: it has a rectangular slot having a small height (dimension in the transverse direction), for example equal to 0.2 mm and a length greater than 2 mm. The small slot height of the detection collimator in the diffraction plane (X,D) contributes to obtaining a good angular resolution since the diffraction angle varies strongly in that plane according to the materials analyzed. On the other hand, the diffraction angle changes very little in the Z direction orthogonal to the diffraction plane. The opening of the detection collimator along the axis Z (slot length of the detection collimator) is advantageous for increasing the signal without losing angular resolution.

The increase in energy resolution obtained by virtue of the method and the device according to the invention makes increasing the sensitivity possible by using a detection collimator qualified as open in the transverse direction, to collect more signal. But, as indicated in the introduction, the inspection volume is then greater, with an increased risk of superposition of materials, which may complicate the interpretation of the spectra obtained.

In a preferred version, in order to solve this problem, the invention provides a method of analyzing a sample of materials in which: before combining and after possible adjusting of the measured spectra Si(E), the fulfillment of at least one criterion is verified, that criterion being termed multimaterial criterion, representing the presence of several layers of material, groups of pixels are formed using results of the preceding verifying step, each group corresponding to a layer of material, different groups corresponding to different layers of material, the combining step is carried out by group, that is to say that the adjusted spectra obtained for the pixels of the same group are combined, for each group formed.

In this preferred version, the diffractometer according to the invention thus comprises in addition:

means for verifying the fulfillment of at least one criterion, termed multimaterial criterion, representing the presence of several layers of materials, means for forming groups of pixels, each group corresponding to a layer of material, different groups corresponding to different layers of material, means for combining spectra by group, adapted, for each group, to selectively combine only the spectra (measured or adjusted) obtained for the pixels of said group.

In this way, it becomes possible to use an open detection collimator (that is to say delimiting the detected beam widely in the transverse direction) to obtain a device that is both sensitive, thanks to that opening, and profiting from good energy resolution thanks to the virtual pixelation of the detector. Advantageously, in this preferred version, the detection collimator has a slot of height greater than 1 mm, preferably greater than 2 mm, for example of the order of 2.5 mm. The great height of the detection collimator slot in the diffraction plane (X, D) gives high sensitivity to the analysis device but tends to degrade is angular and energy resolutions; this defect is compensated for, by virtue of the invention, through the use of a virtually pixelated detector and by the combination by group of the different spectra obtained.

Preferably, the adjusted spectra are momentum transfer spectra $S_i(x)$, obtained by virtue of the formula indicated earlier. The combining means are then adapted to sum the adjusted spectra of the pixels of the same group.

In all that follows, "position in a spectrum of an energy peak or of a local maximum" is used to mean the channel or the energy or the momentum transfer x (this is a case of an adjusted spectrum) corresponding to said peak.

Advantageously and according to the invention, each multimaterial criterion is chosen from among: a significant variation, for example greater than 10%, between two adjacent pixels in the transverse direction, of the position of a first local maximum, defined as being the first peak detected along the x-axis in the adjusted spectra; in what follows, this criterion is called multimaterial criterion of the first local maximum, a significant variation, for example greater than 10%, between two adjacent pixels in the transverse direction, of the position of a second local maximum, defined as being the second peak detected along the x-axis in the adjusted spectra; in what follows, this criterion is called multimaterial criterion of the second local maximum. a significant variation, for example greater than 10%, between two adjacent pixels in the transverse direction, of the sum of the channels of the adjusted spectrum (in other words of the integral of the adjusted spectrum, that is to say of the area delimited by the curve of the adjusted spectrum and the x-axis).

Preferably, to verify the fulfillment of the multimaterial criterion of the first (respectively second) local maximum defined above, a curve is constructed wherein the y-axis represents the position in the spectrum of the first (respectively the second) local maximum and wherein the x-axis represents the lateral position Yi of the pixel Pi or its angle of observation θi. This curve presents at least one "jump", that is to say an increase or a reduction of more than 10% along the y-axis between two adjacent pixels, and thus over a variation in terms of x-coordinates less than a maximum dimension of the pixels in the transverse direction.

Each value Yi of the lateral position in which such a jump is involved is used for forming groups of pixels. All the pixels of which the position lateral Yi (or diffraction angle θi) is comprised between two consecutive jumps are considered as belonging to the same group.

Advantageously and according to the invention, the means for verifying at least one multimaterial criterion are adapted to verify the multimaterial criterion of the first local maximum. In this case, they are preferably adapted to establish a curve wherein the y-axis represents the position in the spectrum of the first local maximum and wherein the x-axis represents the angle of observation θi or the lateral position Yi of the pixel Pi. The means for forming groups of pixels are thus adapted to group together within the same group two adjacent pixels Pi and $P_{i+1}$ in the transverse direction if and only if the difference between the position of the first local maximum in the adjusted spectrum of the pixel Pi and the position of the first local maximum in the adjusted spectrum of the pixel $P_{i+1}$ do not vary by more than 10%.

Advantageously and according to the invention, the means for verifying at least one multimaterial criterion are, as a variant or in addition, adapted to verify the multimaterial criterion of the second local maximum. In this case, they are preferably adapted to establish a curve wherein the y-axis represents the position in the spectrum of the second local maximum and wherein the x-axis represents the angle of observation θi or the lateral position Yi of the pixel Pi. The means for forming groups of pixels are thus adapted to group together within the same group two adjacent pixels Pi and $P_{i+1}$ in the transverse direction if and only if the difference between the position of the second local maximum in the adjusted spectrum of the pixel Pi and the position of the second local maximum in the adjusted spectrum of the pixel $P_{i+1}$ do not vary by more than 10%.

Preferably, the method of analysis according to the invention comprises verifying the fulfillment of two multimaterial criteria.

BRIEF DESCRIPTION OF THE DRAWING

Other details and advantages of the present invention will appear from the reading of the following description, which refers to the diagrammatic appended drawings and which relates to preferred embodiments, provided by way of non-limiting examples. In the drawings:

FIG. 7 represents a simulation of two adjusted diffraction spectra which would be obtained for a sample of aluminum by a diffractometer with a pixelated detector according to the invention, by employing a collimator delimiting the detected beam respectively narrowly (this is then termed a narrow collimator) and widely (this is then termed an open collimator) along the transverse axis defined earlier.

FIG. 8 represents a simulation of bi-parameter spectra in lateral position which would be obtained for a sample of aluminum by a diffractometer with a pixelated detector according to the invention with an open detection collimator. FIG. 8a represents the measured bi-parameter energy spectrum (before adjustment); FIG. 8b represents the adjusted bi-parameter spectrum.

FIG. 9 illustrates a curve representing the position of the first local maximum in relation to the lateral position, and furthermore illustrates a curve representing the position of the second local maximum in relation to the lateral position, of the adjusted spectra of FIG. 8b.

FIG. 10 illustrates a sample of material 100 constituted by two layers of materials, i.e. a layer of graphite and a layer of salt. The inspection volumes observed, respectively by a detector with an open collimator, and by a detector with a narrow collimator, are represented in the FIG.

FIG. 11 represents a simulation of bi-parameter spectra in lateral position which would be obtained for the salt/graphite sample of FIG. 10 by a diffractometer with a pixelated detector according to the invention with an open detection collimator. FIG. 11a represents the measured bi-parameter energy spectrum (before adjustment); FIG. 11b represents the adjusted bi-parameter spectrum.

FIG. 12 illustrates a curve representing the position of the first local maximum according to the lateral position, and furthermore illustrates a curve representing the position of the second local maximum according to the lateral position, of the adjusted spectra of FIG. 11b.

FIG. 13 represents a simulation of adjusted diffraction spectra which would be obtained for the salt/graphite sample of FIG. 10 by a diffractometer with a pixelated detector according to the invention and with an open detection collimator. A first spectrum corresponds to the spectrum obtained by combination of all the spectra for the pixels of the detector; a second spectrum corresponds to the spectrum obtained by combination of the spectra of the pixels of the detector having a lateral position comprised between 0 and 1 mm; the third spectrum corresponds to the spectrum obtained by combination of the spectra of the pixels of the detector having a lateral position comprised between 1 mm and 2.5 mm.

DETAILED DESCRIPTION

Figure 1:
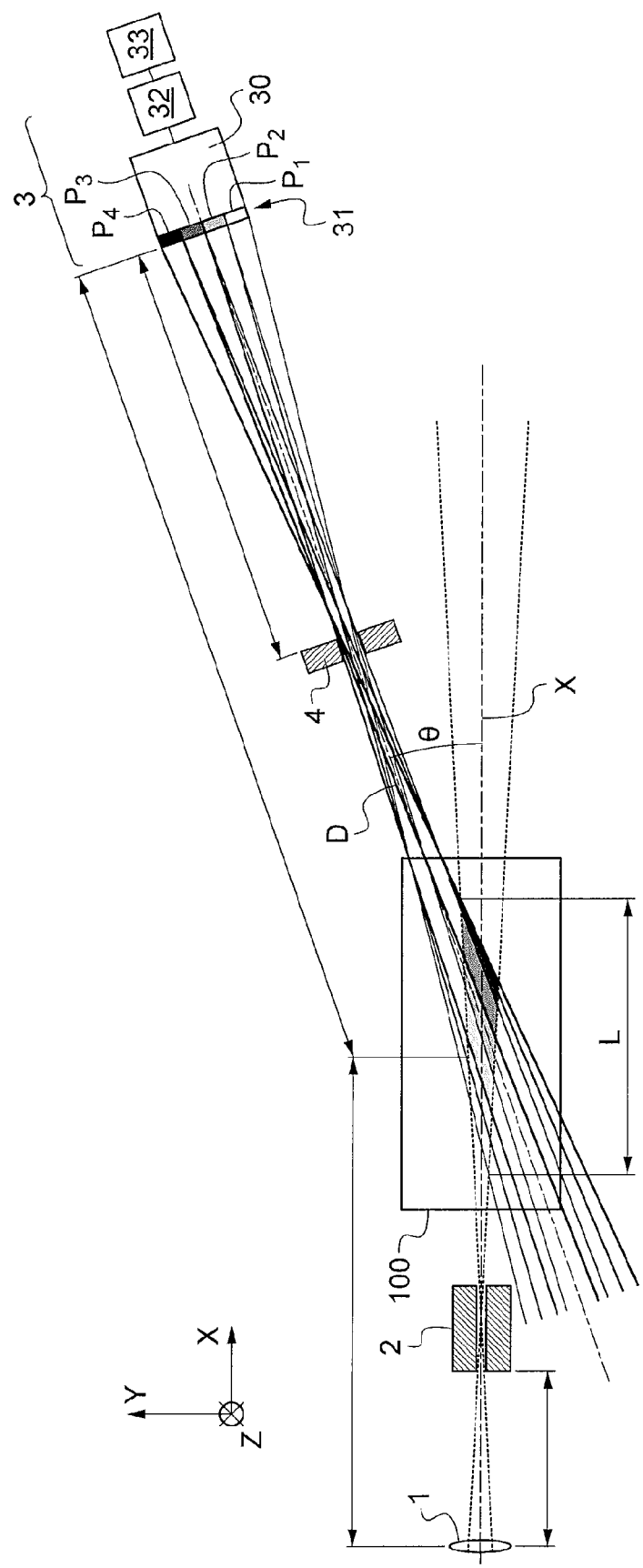
FIG. 1 is a diagrammatic view in cross-section in a diffraction plane of a diffractometer according to the invention.

FIG. 1 illustrates a diffractometer according to the invention. This comprises first of all a polychromatic source 1 of energy comprised between a few tens of keV and a few hundred keV, for example between 10 keV and 200 keV. This source 1 emits radiation that is collimated using a source collimator 2, it being possible for the latter to be produced from tungsten or tungsten alloy. As non-limiting illustrated example, this source collimator 2 has a single rectangular slot and a thickness of 100 mm and a slot height less than 0.5 mm; for example equal to 0.1 mm. It is disposed at a distance from the source 1 equal to 140 mm. The polychromatic source 1 and the source collimator 2 generate an incident beam with an axis X. The diffractometer according to the invention next has an accommodation for receiving a sample of material 100, that accommodation being formed such that the sample of material is irradiated by the incident beam generated by the source 1 and the source collimator 2. The diffractometer according to the invention further comprises a detector collimator 4 and a detector 3, which are aligned along a detection axis D forming with the axis X of the incident beam an angle θ here equal to 4 (the appended FIG.s are not to scale).

The detector 3 comprises a detector material 30, which, facing the detector collimator 4, presents a detection plane 31, and further comprises electronic and computer processing means 32 and 33. Preferably, the detector material 30 used here is a semiconductor material such as a material based on CdTe, CdZnTe (CZT), silicon (Si) or Hgl2, capable of being polarized by a cathode and an anode, that are disposed on two opposite faces of the semiconductor material. It is also possible to employ a Germanium-based detector, despite the constraints described earlier. When a photon penetrates the semiconductor material 30 and interacts with it, all or some of its energy is transferred to charge carriers (electron/hole pairs) in the semiconductor material. Because the detector is polarized, the charge carriers migrate towards the electrodes (including the anode). They then produce an electrical signal at the terminals of the electrodes. This electrical signal, the amplitude of which is proportional to the energy deposited by the photon at the time of the interaction, is collected then processed by the computer means 32 and 33. The signal is preferably collected solely at the anode; it may as a variant be collected solely at the cathode, or at both electrodes. A detector with a semiconductor material usually comprises a plurality of physical pixels, each physical pixel corresponding to a circuit for charge collection by an electrode. The full pixel Pc illustrated in FIG. 2 corresponds to a physical pixel of the known diffractometer.

According to the invention, the detector 3 is a virtually pixelated detector in order to obtain fine pixelation and a large improvement in the angular resolution, which means that the detection plane 31 of the semiconductor material 30 is provided with physical pixels that are divided into virtual pixels $P_i$. (cf. FIGS. 1 to 3).

In the illustrated example, the detection plane 31 has four columns of pixels each comprising four pixels ($P_1$ to $P_4$ for the first column, $P_5$ to $P_8$ for the second, etc.) which succeed each other in the transverse direction T which is orthogonal to the detection axis D. Only four rows of pixels (and four columns) are represented here in the interest of clarity, but it is of course possible for there to be more. Each of these virtual pixels $P_i$ observes a volume of material of length (along the axis X) equal to 17.5 mm and detects the radiation diffracted at an average angle $\theta_i$ which can be seen more easily in FIG. 3, that is to say the radiation diffracted between the angles $\theta_i - \delta\theta/2$, and $\theta_i + \delta\theta/2$ with $\delta\theta$ being of the order of 0.2°. as illustrated in FIG. 4. A full pixel Pc corresponding to the sixteen pixels $P_1$ to $P_{16}$ of the detector of the diffractometer according to the invention would detect the radiation diffracted around 4° over a range of diffraction angles three times wider than that attributed to each pixel $P_i$, the criterion chosen to quantify the width of a peak here being the width at mid-height of that peak.

It follows that the angular resolution of the detector of the diffractometer with a pixelated detector according to the invention is much better than that of a known diffractometer for which the detector is provided with the full pixel Pc. This directly results in an improvement in energy resolution of the detector.

The pixelation of the detection plane 31 is obtained here virtually. A mere reduction in the size of the physical pixels would as a matter of fact pose various problems. In particular, the manufacturing costs would be considerably increased; the increased number of electronic processing channels would also adversely affect the manufacturing costs and would lead to production of a bulky device. The pixelation of the detection plane 31 may be obtained virtually using an item of location information for location, within each physical pixel, of a photon interaction taking place in alignment with that pixel. As taught by the publication "*An approach to sub-pixel spatial resolution in room temperature X-ray detector arrays with good energy resolution*" (W. K. Warburton), it is for example possible to determine the coordinates (x, y) of the barycenter of the charge cloud produced by an interaction, based on electrical signals generated simultaneously by that interaction on a plurality of adjacent anodes. This approach makes it possible to divide each physical pixel into a plurality of virtual pixels in the detection plane. It is thus considered that the interaction has been detected solely by the virtual pixel corresponding to the coordinates of the barycenter. In such a method, only the coordinates of the physical pixel that collected the maximum signal are used.

Figure 2:
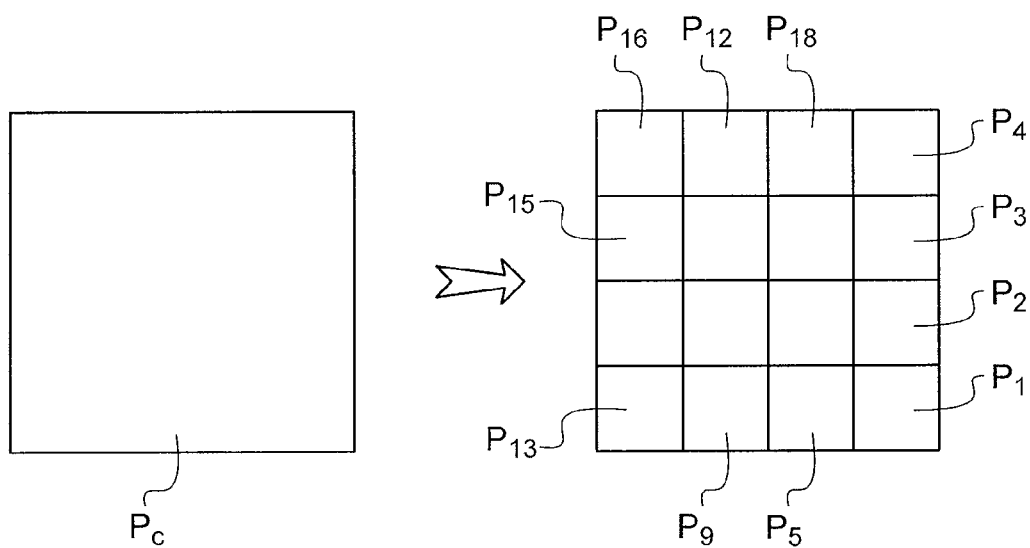
FIG. 2 is a diagrammatic head-on view of the detection plane (right half of the FIG.) of the detector of FIG. 1 and of the corresponding full pixel (left half of the FIG.).
Figure 3:
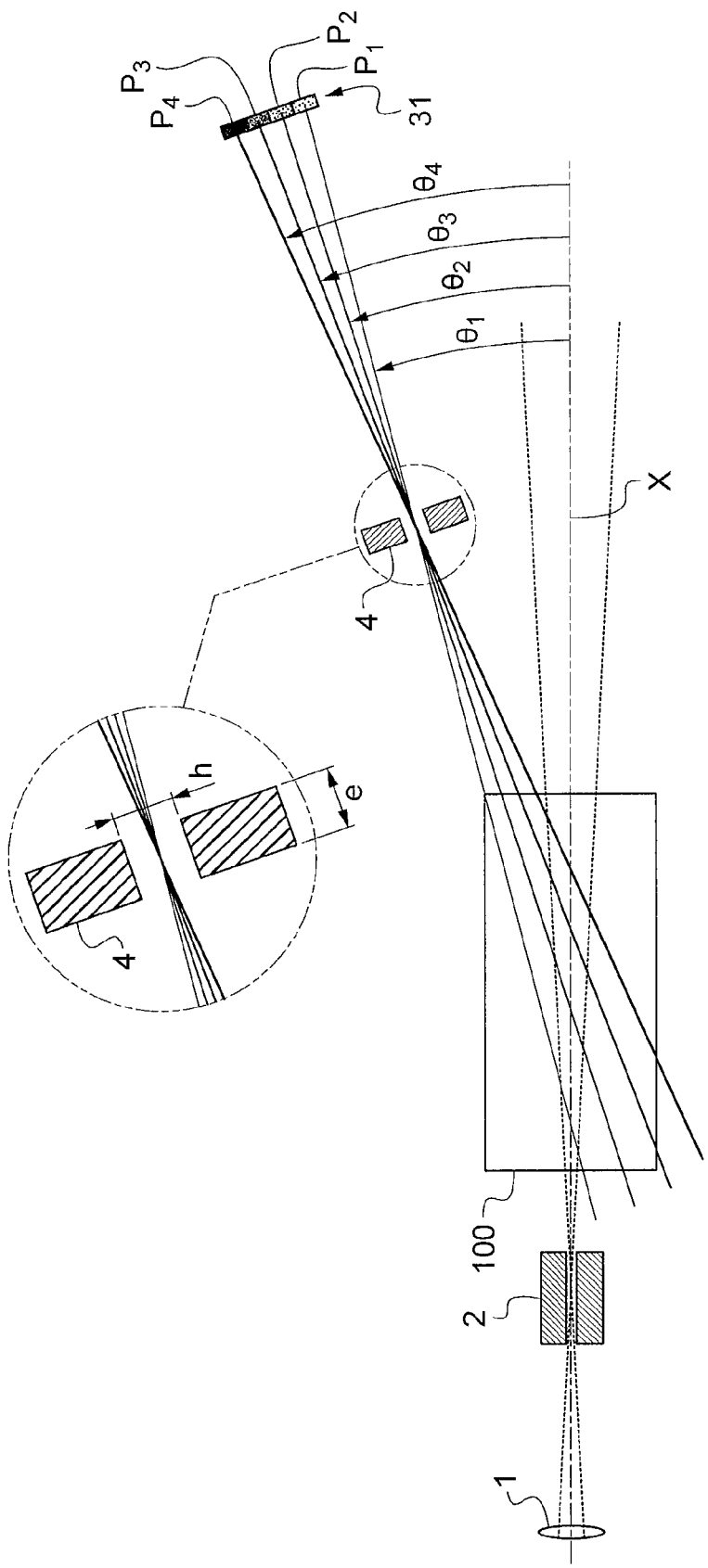
FIG. 3 adopts the diagrammatic view of FIG. 1 while providing a few further details therein.
Figure 4:
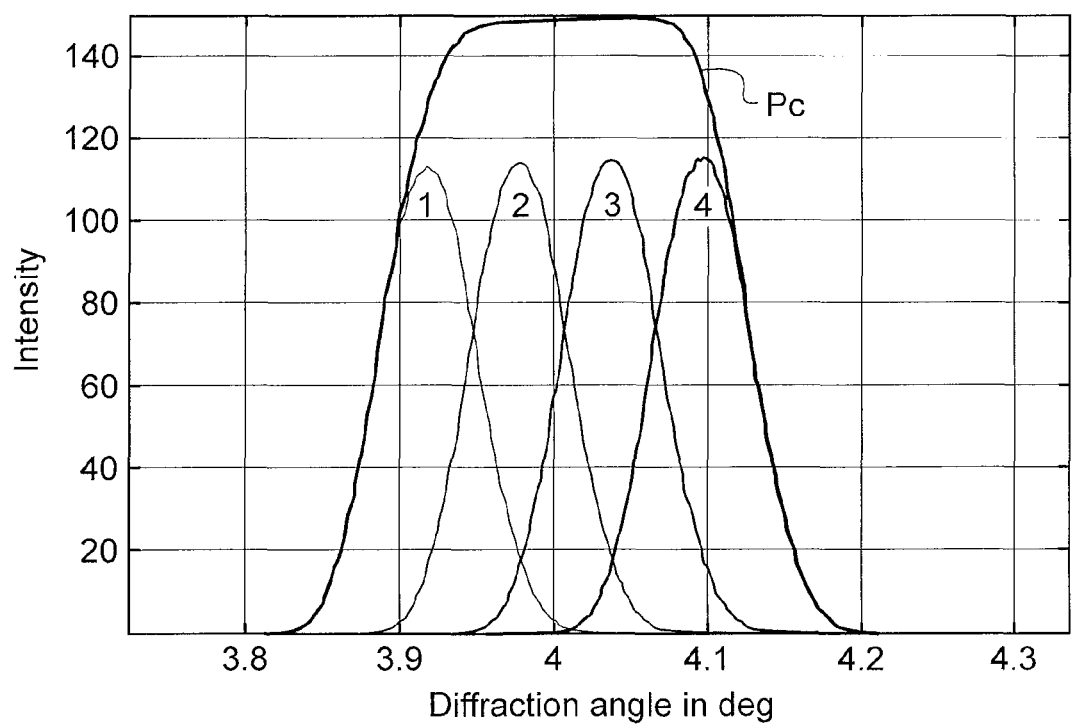
FIG. 4 illustrates the angular resolution observed for each of the virtual pixels of the diffractometer with a pixelated detector of FIGS. 1 to 3, and also illustrates the angular resolution observed for a full pixel corresponding to that diffractometer.

The diffractometer according to the invention illustrated in FIGS. 1 to 3 makes it possible to observe, in the sample of material 100, an inspection volume of length L which depends on the opening of the detector collimator 4. If the detector collimator 4 is a narrow collimator, having for example a slot height of 0.4 mm, which corresponds to a diffraction range $\Delta\theta$ of 0.3°, the inspection volume is 63.5 mm³ and the inspection length (along the axis X) is 43 mm. If the detector collimator 4 is an open collimator, having for example a slot height of 2.5 mm, which corresponds to a diffraction range $\Delta\theta$ of 1.6°, the inspection volume is 210 mm³ and the inspection length is 139 mm. The use of such an open detector is possible here by virtue of the increase in resolution obtained by the use of a virtually pixelated detector.

Figure 5A:
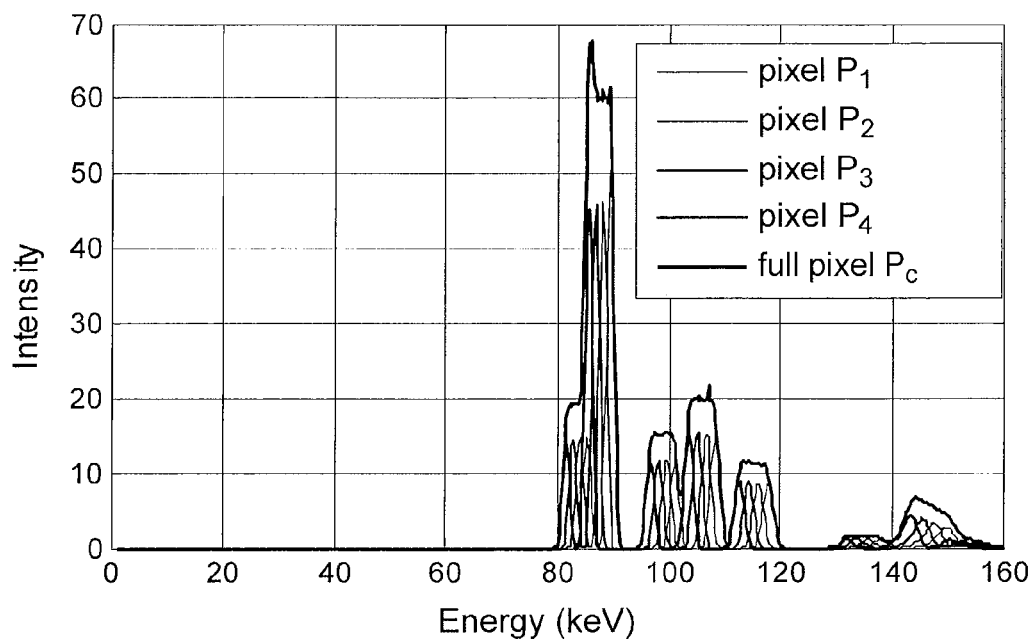
FIG. 5 represents a simulation of the diffraction spectra which would be obtained for graphite by a diffractometer with a pixelated detector according to the invention and by a full pixel corresponding to that detector; More particularly, FIG. 5A concerns a detector assumed to be perfect that is to say a detector of which the resolution σdet is zero; whereas FIG. 5B concerns a detector of resolution σdet equal to 2 keV.
Figure 5B:
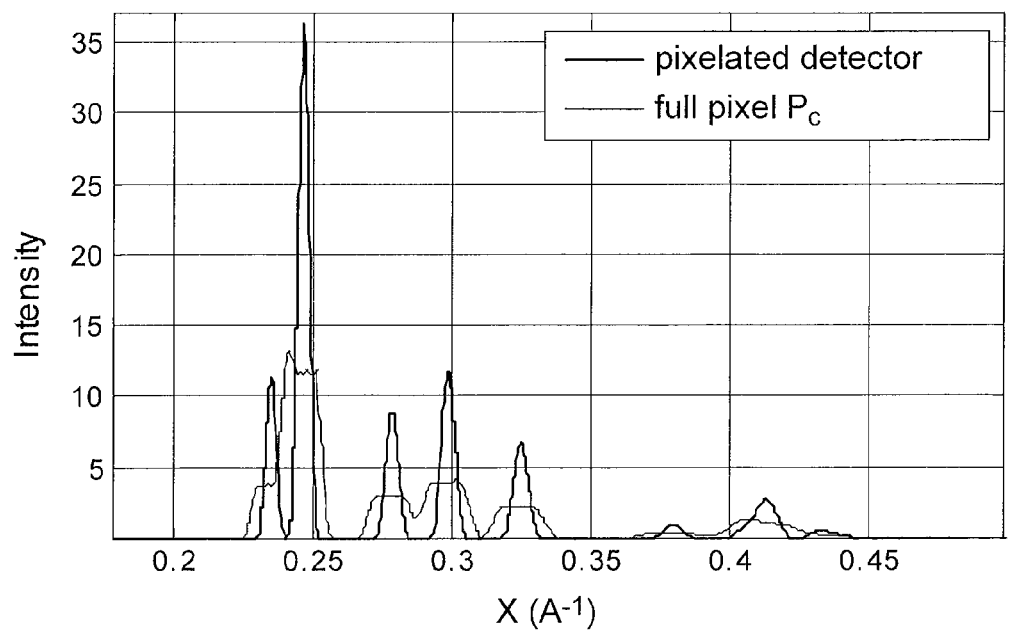

FIG. 5A illustrates the energy spectra obtained by simulation for each of the pixels $p_1$ to $P_4$ of the detector and for the full pixel Pc corresponding to that detector. FIG. 5B represents the combination according to the invention, by the combining means 33, of the energy spectra obtained for the different pixels $P_i$. Prior to this combination, an adjustment is advantageously carried out preferably consisting of: a change in variable making it possible to pass, for each pixel Pi of row i constituting the detector, the latter corresponding to the full pixel Pc, from an energy spectrum to a momentum transfer spectrum (the use of another variable is however possible). It is to be recalled that an energy spectrum is a diagram representing the number of photon interactions found according to the energy E, expressed in keV, released by the interaction; whereas a momentum transfer spectrum is a diagram representing the number of interactions found according to the momentum transfer x, expressed in $nm^{-1}$, of the interaction. As previously observed, the new variable x is obtained according to the energy E and the observation angle $\theta i$ corresponding to the pixel Pi of row i. For example, this change in variable is governed by the following equation:

$$x = \frac{\sin(\theta_i/2)}{\lambda} = \frac{E\sin(\theta_i/2)}{hc}$$

On account of the change in variable, each spectrum Si(E) corresponding to a pixel of row i is transformed into a spectrum Si(x).

The sum of all the spectra so transformed, that is to say of all the momentum transfer spectra Si(x) is established beforehand.

As may be observed in FIG. 5B, this combination (adjustment and summing of the spectra), associated with the virtual pixelation of the detector (which increases the quantity of signals generated, for the same diffraction angle), makes it possible, relative to the spectrum obtained by a full pixel, to obtain diffraction peaks that are more intense and narrower, with deeper troughs, which facilitates the identification of these characteristic rays. In other words, the energy resolution is appreciably improved. At the same time, it is found that the area delimited by the curve of the spectrum of the pixelated detector is substantially the same as that delimited by the spectrum of the full pixel. The sensitivity (total quantity of photons detected) is thus maintained, which appears prima facie incompatible with an increase in energy resolution, the improvement of one of these parameters generally resulting in the deterioration of the other. It is also to be noted that, as regards the simulation here, no background noise appears on the illustrated spectra. The person skilled in the art will easily understand that in the case of measured spectra, with background noise, the invention even makes it possible to simultaneously improve sensitivity (on account of a reduced detection limit) and energy resolution.

FIG. 7 represents a simulation of two diffraction spectra. A first spectrum 702 is obtained for a sample of aluminum by the diffractometer of FIGS. 1 to 3, using a narrow collimator (h=0.4 mm). A second spectrum 701 is obtained on that same sample, using an open collimator (h=2.5 mm). In order not to degrade the energy resolution, these spectra are adjusted.

As may be noted on examination of that FIG., the diffraction peaks obtained with the open detection collimator are much greater and more legible than those obtained with the narrow detection collimator. This FIG. illustrates the increase in sensitivity obtained by passing from a narrow collimator to an open collimator, this being without loss in energy resolution. The use of a detector pixelated finely and virtually thus makes opening of the collimation possible in order to improve the sensitivity of the device, since it compensates for the loss in energy resolution of the diffraction peaks which results therefrom.

However, the opening of the detection collimator is accompanied by an enlargement of the inspected volume; there is then a high risk of the inspection volume comprising several layers, as illustrated by FIG. 10. This FIG. 10 represents a sample of material 100 comprising a layer 101 of graphite and a layer 102 of salt. The inspection volume 201 is that observed by the narrow collimator (h=0.4 mm); it only comprises salt. The inspection volume 200 corresponds to that observed by the open collimator (h=2.5 mm), it comprises graphite and salt.

In a preferred version of the invention, a second important feature is the combination of the spectra by group which makes it possible to get round the problem of confusion of the materials in the spectra obtained.

Prior to this combination, it is advantageous to perform adjustment of the measured energy spectra as explained earlier.

FIG. 8a represents energy spectra measured for a monomaterial sample entirely constituted by aluminum. FIG. 8b represents the corresponding adjusted spectra. These representations are qualified as bi-parameter representations. The x-axis of FIG. 8a represents, as is conventional in spectrometry, the energy E released by the photon interactions detected. The x-axis of FIG. 8b represents the momentum transfer x. But, in an original way, the energy intensity (that is to say the number of interactions detected for each energy or for each momentum transfer) is not represented on the y-axis but using grayscale. The light areas of the graph show low intensity, contrary to the dark areas which correspond to the diffraction peaks. The y-axis may then be used for another parameter, i.e. the lateral position Yi of the pixel Pi in the detector (position in the transverse direction T). In the same FIG. are thus represented all the measured (FIG. 8a) or adjusted (FIG. 8b) energy spectra obtained for all the pixels of the detector: to each y-coordinate corresponds the spectrum of a pixel. Visually scanning the y-axis amounts to moving in the detector in the direction T. To better understand the adopted representation, it suffices to imagine it in three dimensions. A "cross-section" of the graph at a given lateral position Y corresponds to an "conventional 2D" energy spectrum such as that of FIG. 3.

FIG. 8 illustrates the measured and adjusted spectra obtained for a monomaterial sample constituted entirely of aluminum. FIG. 11 illustrates the spectra measured and adjusted which were obtained for a multimaterial sample comprising a layer of graphite and a layer of salt; this is the sample 100 illustrated in FIG. 10.

The combination of the adjusted spectra is carried out by group in a preferred version of the invention, it is thus required to form groups of pixels according to the layers of materials present in the sample.

For this, it is appropriate first of all to determine whether the sample comprises several layers of different materials. To that end, the fulfillment is verified of one or more multimaterial criteria representing the presence of several layers of materials. One of those criteria may be the variation in the adjusted spectra of the position of the first local maximum.

In the bi-parameter spectra of FIGS. 8 and 11, the first local maximum may be identified by the grayscales used: the darkest gray corresponds to the most intense diffraction peak. The first local maximum for a given pixel thus corresponds to the first zone of dark gray surrounded by lighter gray that is encountered on scanning the spectrum along the x-axis at constant y-coordinate.

In the spectra of FIG. 8 which correspond to a monomaterial sample, it is found that the position of the first local maximum does not vary or varies little according to the lateral position: the zones of darker gray are vertically aligned; they correspond to the same momentum transfer for all the pixels.

In the spectra of FIG. 11 which correspond to a graphite/salt multimaterial sample, it is found that the position of the first local maximum varies according to the pixels. It is noted that, for the pixels whose lateral position is comprised between 0 and approximately 1 mm (upper part of the FIG.), the first local maximum is obtained for a momentum transfer x of the order of 2 $nm^{-1}$, whereas for the pixels whose lateral position is greater than 1 mm (lower part of the FIG.), the first local maximum is obtained for a momentum transfer x of the order of 2.3 $nm^{-1}$.

To determine with greater certainty and precision if a change in position of the first local maximum has taken place and, the case arising, at what lateral position Yi (that is to say at what pixel Pi) it took place, a curve is constructed representing the position of the first local maximum according to the lateral position.

This curve 901 is plotted in FIG. 9 for the monomaterial sample of aluminum; it confirms that the position of the first local maximum varies little according to the pixels: the curve 901 obtained is relatively flat.

The curve for the graphite/salt multimaterial sample can be seen in FIG. 12. The curve 1201 obtained shows a steep slope for a lateral position close to 1 mm (of the order of 0.9): the first local maximum varies (drops) there by more than 10% in less than 0.2 mm.

To confirm or possibly refine these results, it is advantageous to verify the fulfillment of a second multimaterial criterion, for example also to study the variation in the position of the second local maximum. The corresponding curves are obtained and represented respectively in FIG. 9 (curve (902)) and in FIG. 12 (curve 1202) in similar manner to those relative to the first local maximum. In the case of the monomaterial sample (FIG. 9), a curve close to a straight line of zero slope is found. In the case of the graphite/salt multimaterial sample (FIG. 12), a significant jump is again observed for a lateral position Yi equal to 1 mm.

Figure 6A:
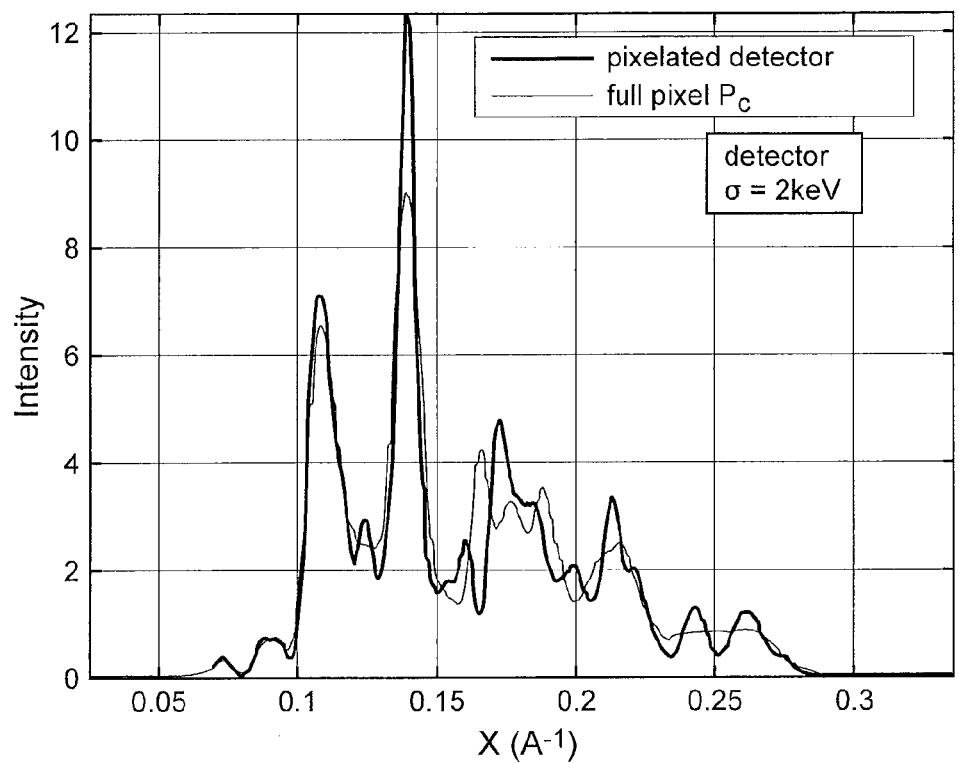
FIG. 6 represents a simulation of the diffraction spectra which would be obtained for sugar by a diffractometer with a pixelated detector according to the invention and by a full pixel corresponding to that detector; More particularly, FIG. 6A concerns a detector of resolution σdet equal to 2 keV; whereas FIG. 6B concerns a detector of resolution σdet equal to 4 keV.
Figure 6B:
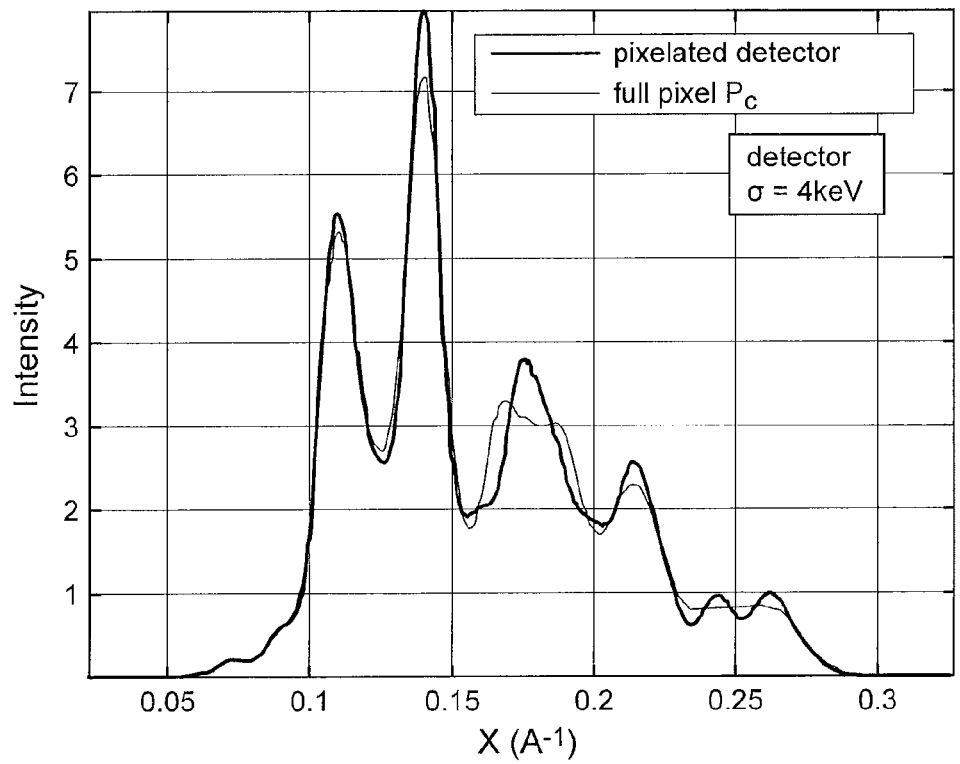

The lateral positions around which a significant variation (jump of the curves 1201, 1202) from the position of the first and/or the second local maximum is observed, are recorded as constituting the bounds of the groups of pixels. Thus, in the example of the graphite/salt multimaterial sample of FIG. 6, all the pixels for which the lateral position is comprised between 0 and 1 mm are considered as belonging to the first group representing a first material (in this case, graphite); the pixels for which the lateral position is greater than 1 mm are considered as belonging to a second group representing a second material (in this case, salt). In the example of the monomaterial sample of aluminum, the multimaterial criteria not being verified (which means that only one material has been detected), only one group containing all the pixels of the detector is formed.

The adjusted spectra are next summed by group.

FIG. 13 illustrates three combinations of momentum transfer spectra obtained for the graphite/salt multimaterial sample of FIG. 10: the spectrum 1301 corresponds to the sum of the adjusted spectra of all the pixels of the detector; the spectrum 1302 corresponds to the sum of the adjusted spectra of the pixels of the first group defined above (group corresponding to graphite); the spectrum 1303 corresponds to the sum of the adjusted spectra of the pixels of the second group defined earlier (group corresponding to salt).

As can be seen in this FIG. 13, the combination (sum after adjustment) by group, associated with the virtual pixelation of the detector (which increases the quantity of signals generated), makes it possible, relative to the spectrum 1301 obtained for the whole detector:

to separate the peaks into groups, which facilitates the interpretation of the spectra: considering that two peaks which are in reality due to two distinct materials, correspond to the same material, and thus being mistaken in the identification of the material or materials present, is thus avoided, and to obtain diffraction peaks that are more intense and narrower, with deeper troughs, which facilitates the identification of the characteristic rays. In other words, the energy resolution is appreciably improved.

It is also to be noted that, as regards the simulations here, no background noise appears on the illustrated spectra. The person skilled in the art will easily understand that in the case of spectra that are really measured, with background noise, the invention even makes it possible to simultaneously increase sensitivity (on account of the reduced detection limit) and energy resolution, and that it furthermore makes it possible, in its preferred version, to detect the presence of several materials and to reliably define the nature thereof.

The invention may be the object of numerous variants relative to the embodiment illustrated, provided those variants enter the scope delimited by the claims. In particular, the detector may be constituted by a greater number of virtual pixels distributed in several directions, for example in two directions in the detection plane (as in the illustrated example), and possibly also the direction of the thickness. As the diffraction at a given angle θ takes place in all the directions around the axis X of the incident beam in a cone (of angle θ), the pixelation of the detection plane in two orthogonal directions makes it possible to refine the angular resolution over the whole of the portion of that cone captured by the detector and to increase further still the quantity of signal that is available and processed. In general terms, the row i of the pixel Pi thus varies between 1 and Imax, Imax being the number of virtual pixels that the detection plane comprises.

In the example described above, the multimaterial criterion is established by determining the position of the first or second peaks on the adjusted spectra. Other types of criteria may be implemented. For example, the integral $I_i$, that is to say the sum of the channels, may be determined, for each spectrum $S_i$ obtained and it may be concluded that several materials are present when that integral varies significantly, for example by more than 10%, between two adjacent pixels.

Furthermore, the geometry of the diffractometer is not limited to the numerical values provided above. In addition, other methods for combining spectra, relating to spectra adjusted according to a variable (which depends on the energy E or the wavelength λ, as well as the diffraction angle) other than the momentum transfer, may be used.

The invention may be the object of numerous variants relative to the embodiment illustrated, provided those variants enter the scope delimited by the claims. In particular, the detector may be constituted by pixels distributed in several directions, for example in two directions in the detection plane, such as is illustrated in FIG. 2, and possibly also the direction of the thickness. As the diffraction at a given angle θ takes place in all the directions around the axis X of the incident beam in a cone (of angle θ), the pixelation of the detection plane in two orthogonal directions makes it possible to refine the angular resolution over the whole of the portion of that cone captured by the detector and to increase further still the quantity of signal that is available and processed. In general terms, the row i of the pixel $P_i$ thus varies between 1 and $I_{max}$, $I_{max}$ being the number of pixels, virtual or physical, constituting the detector in the zone delimited by the solid angle by which the detector sees the inspection volume.

Furthermore, the geometry of the diffractometer is not limited to the numerical values provided above. The degree of pixelation (fractioning of the full pixel) of the detector according to the invention may be greater or possibly less than that illustrated in FIG. 2. Furthermore, other methods of combining energy spectra may be used, the protected provided in the illustrated example having the advantage of being simple and fast.

The invention claimed is:

1. A method of analyzing a sample of material by diffractometry, the method comprising:
   providing a diffractometer that comprises:
      a source adapted to emit an incident beam with a central axis,
      a detector that includes
   a detector material having a detection plane a proximate to the sample of material,
   spectrometry measurement means, adapted to measure an energy released by each photon interaction with the detector material and to establish at least one energy spectrum S(E); and
      a detection collimator associated with the detector, the detector and the detection collimator arranged so as to have a detection axis D forming a diffraction angle θ with the central axis X of the incident beam; and
   irradiating the sample with the incident beam;
   establishing a plurality of energy spectra; and
   combining the energy spectra,
   wherein the detector comprises a pixelated detector including means for locating an interaction of a photon with the detector material, and
   the method further comprises:
   defining a partition of the detector in virtual pixels, and associating one of the virtual pixels with each photon interaction;
   establishing a measured energy spectrum Si(E) for each virtual pixel (Pi) of the detector; and
   combining energy spectra measured for different virtual pixels (Pi) of the detector.

2. A method according to claim 1, wherein the detector comprises a detector having a pixelated detection plane.

3. A method according to claim 1, wherein a pitch between two adjacent pixels in a transverse direction orthogonal to the detection axis D and contained in a diffraction plane (X, D), is less than or equal to 0.5 mm.

4. A method according to claim 1 further comprising, prior to combining the energy spectra, adjusting the measured energy spectra, where each measured energy spectrum Si(E) is expressed according to a new variable (x) which takes into account an energy of scattered radiation and an angle of observation $\theta_i$ of the corresponding pixel, and obtaining an adjusted spectrum Si(x) for each pixel (Pi) of the detector.

5. A method according to claim 4, wherein,
in adjusting the measured energy spectra, for each pixel (Pi), a spectrum Si(x) is established which is adjusted according to momentum transfer based on the energy spectrum measured for the pixel, by performing a change in variable according to the formula:

$$x = \frac{\sin(\theta_i/2)}{\lambda} = \frac{E\sin(\theta_i/2)}{hc}$$

where $\theta_i$ is the observation angle corresponding to the pixel Pi and $\lambda$ is the wavelength corresponding to the energy E, and
in combining the energy spectra, a sum is calculated of at least some of the momentum transfer of the spectrum Si(x).

6. A method according to claim 4, wherein before combining the energy spectra and after adjusting the measured energy spectra, verifying at least one multimaterial criterion representing the presence of several layers of material, the method further comprising
forming groups of pixels using results of the verifying step, each group corresponding to a layer of material, where different groups correspond to different layers of material, and
wherein combining the energy spectra is carried out by group, such that the adjusted energy spectra obtained for the pixels (Pi) of the same group are combined.

7. A method according to claim 4, wherein
in adjusting the measured spectra, the adjusted spectra comprise momentum transfer spectra Si(x), the change in variable is carried out using the formula:

$$x = \frac{\sin(\theta_i/2)}{\lambda} = \frac{E\sin(\theta_i/2)}{hc},$$

where $\theta_i$ designates the diffraction angle corresponding to the pixel Pi such that the angle between the axis X of the incident beam and the axis Di passing by the center of the pixel Pi and the center of the detection collimator, and $\lambda$ is the wavelength corresponding to the energy E; and
in combining the energy spectra, for each group, the adjusted spectra Si(x) of the pixels of the group are summed.

8. A method according to one of claim 6, wherein the multimaterial criterion comprises one of:
a variation greater than 10% of the position in the adjusted spectra of a first local maximum, between two adjacent pixels in a transverse direction (T), orthogonal to the detection direction (D), or
a variation greater than 10% of the position in the adjusted spectra of a second local maximum, between two adjacent pixels in the transverse direction, or
a variation greater than 10% of the sum of the channels of the adjusted spectrum of each pixel, between two adjacent pixels in the transverse direction.

9. A method according to claim 8 further comprising constructing a curve, wherein the y-axis represents the position in the spectrum of the first or second local maximum and wherein the x-axis represents the lateral position (Yi) of the pixel (Pi) or its angle of observation ($\theta$i).

10. A method according to claim 6, wherein the detection collimator comprises an open collimator having a slot with a height greater than 1 mm.

11. A diffractometer comprising:
a source adapted to emit an incident beam with a central axis X;
a detector comprising
a detector material having a detection plane proximal to a sample material;
spectrometry measurement means, adapted to measure an energy released by each photon interaction with the detector material and to establish at least one energy spectrum;
a detection collimator associated with the detector, the detector and the detection collimator being arranged so as to have a detection axis D forming a diffraction angle $\theta$ with the central axis X of the incident beam; and
spectra combining means, wherein:
the detector comprises a pixelated detector comprising means for locating an interaction of a photon with the detector material, and defining a partition of the detector in virtual pixels, and associating one of the virtual pixels with each photon interaction;
the spectrometry measuring means are adapted to establish an energy spectrum Si(E) for each pixel (Pi) of the detector,
the combining means are adapted to combine energy spectra Si(E) obtained for different pixels Pi of the detector.

12. A diffractometer according to claim 11, wherein the detector comprises a detector having a pixelated detection plane.

13. A diffractometer according to one of claim 12, wherein the pitch between two adjacent pixels in a transverse direction orthogonal to the detection axis D and contained in a diffraction plane (X, D), is less than or equal to 0.5 mm.

14. A diffractometer according to one of claim 11, further comprising computing adjusting means adapted to establish, for each measured energy spectrum S(E), an adjusted spectrum expressed according to a variable which takes into account the energy of the scattered radiation and the diffraction angle $\theta$i.

15. A diffractometer according to claim 14, wherein the adjusting means are adapted to establish, for each pixel (Pi), a momentum transfer spectrum Si(x) based on the energy spectrum measured for the pixel by performing a change in variable by the formula:

$$x = \frac{\sin(\theta_i/2)}{\lambda} = \frac{E\sin(\theta_i/2)}{hc}$$

where $\theta_i$ designates the observation angle of the pixel i (Pi) and $\lambda$ is the wavelength corresponding to the energy E, and
the combining means are adapted to sum spectra so adjusted.

16. A diffractometer according to claim 11, wherein the detector material comprises a semiconductor detector material.

17. A diffractometer according to claim 11, wherein the diffraction angle θ is between 2° and 10°.

18. A diffractometer according to claim 17, wherein the diffraction angle θ is between 3° and 6°.

19. A diffractometer according to claim 11, wherein the source comprises a polychromatic source, and producing radiation having a maximum energy of between 10 and 200 keV.

20. A diffractometer according to claim 11, wherein the detection collimator includes a single rectangular slot having a height of 0.2 mm and a length of 2.5 mm.

21. A diffractometer according to claim 11 further comprising:
    means for verifying the fulfillment of at least one multimaterial criterion, representing the presence of several layers of materials,
    means for forming groups of pixels, each group corresponding to a layer of material, different groups corresponding to different layers of material,
    wherein the combining means are adapted to combine spectra by group, such that for each group, the spectra obtained are combined for the pixels of the group.

22. A diffractometer according to claim 21, wherein:
    the means for verifying at least one multimaterial criterion are adapted to establish a curve representing the position of a first local maximum in the adjusted spectrum of a pixel Pi, along the y-axis, according to, along the x-axis, an angle of diffraction θi of the pixel Pi or a lateral position Yi thereof defined as being a coordinate of the pixel Pi in a transverse direction (T), orthogonal to the detection axis D and contained in a detection plane (X,D),
    the means for forming groups of pixels are adapted to group together within the same group two adjacent pixels $P_i$ and $P_{i+1}$ in the transverse direction if and only if the difference between the position of the first local maximum in the spectrum of the pixel $P_i$ and the position of the first local maximum in the spectrum of the pixel $P_{i+1}$ do not vary by more than 10%.

23. A diffractometer according to claim 21, wherein the detection collimator comprises an open collimator including a slot having a height (h) greater than 1 mm.

24. A method according to claim 1, wherein a pitch between two adjacent pixels in a transverse direction orthogonal to the detection axis and contained in a diffraction plane is less than or equal to 0.2°.

25. A diffractometer according to one of claim 12, wherein the pitch between two adjacent pixels in a transverse direction orthogonal to the detection axis D and contained in a diffraction plane (X, D), is less than or equal to 0.2°.

* * * * *